United States Patent [19]

Fischer et al.

[11] Patent Number: 4,716,893
[45] Date of Patent: Jan. 5, 1988

[54] BONE FASTENER

[75] Inventors: Artur Fischer, Weinhalde 34, D-7244 Tumlingen/Waldachtal; Wolfgang Kramer, Oberjettingen, both of Fed. Rep. of Germany

[73] Assignee: Artur Fischer, Tumlingen, Fed. Rep. of Germany

[21] Appl. No.: 813,221

[22] Filed: Dec. 23, 1985

[30] Foreign Application Priority Data

Mar. 11, 1985 [DE] Fed. Rep. of Germany ....... 3508567

[51] Int. Cl.$^4$ .............................................. A61F 5/04
[52] U.S. Cl. .............................................. 128/92 YF
[58] Field of Search ............ 128/92 YF, 92 R, 92 YP; 411/57, 60, 71, 72, 128, 395

[56] References Cited

U.S. PATENT DOCUMENTS 3,896,504  7/1975  Fischer .......................... 128/92 YF
4,611,581  9/1986  Steffee ................................... 128/69

Primary Examiner—C. Fred Rosenbaum
Assistant Examiner—C. W. Shedd
Attorney, Agent, or Firm—Michael J. Striker

[57] ABSTRACT

A fastener for anchoring in a bore in a bone has a screw extending along an axis and having a substantially cylindrical outer surface formed with a helical screwthread. The screw has at the screwthread a thread diameter and between the turns of the thread at the surface a root diameter smaller than the thread diameter. An anchor sleeve normally fitted in the bore and of an outside diameter corresponding generally to the diameter of the bore has an outer end formed with a laterally projecting rim normally lying against the bone around the bore, an outer end portion of an inside diameter greater than the root diameter but smaller than the thread diameter, and an inner end portion of an inside diameter smaller than the root diameter. Thus when the screw is threaded into the sleeve its thread cuts into the outer portion without substantially deforming and spreading same and into the inner portion with substantial outward deformation and spreading of same.

7 Claims, 2 Drawing Figures

BONE FASTENER

FIELD OF THE INVENTION

The present invention relates to a bone fastener. More particularly this invention concerns a screw-type fastener of the type used to anchor a splint plate or the like to a bone or to secure bone fragments together.

BACKGROUND OF THE INVENTION

A standard orthopedic procedure, for instance to splint the lateral portion of the distal tibia, entails reducing the fracture, drilling at least one hole to each side of the fracture, and then securing a plate across the fracture with screws. Similarly it is known, for example to fix a fragment of a broken medial malleolus, to drill a hole through the fragment into the bone and secure the fragment in place with a screw. The type of screw used depends on the type of bone tissue they will have to hold in. Cortical screws are intended to hold at the hard outer cortex of the bone while cancellous screws hold in the soft interior of the bone.

Thus a cancellous screw has a very deep screwthread intended to bite into the spongy interior of the bone. Unfortunately, once the fracture has knitted, this type of screw is fairly difficult to remove due to the adhesion of the spongy bone to its considerable surface are. In addition the hold of such a screw is frequently poor as the material it is holding in has little elasticity so when stressed the screw either holds solidly or comes completely loose. The screw can loosen or pull out if stressed beyond a predetermined relatively low limit, there being no elastic give to the connection.

OBJECTS OF THE INVENTION

It is therefore an object of the present invention to provide an improved screw-type bone fastener.

Another object is the provision of such a bone fastener screw which overcomes the above-given disadvantages, that is which holds very solidly and with some elasticity yet which is relatively easy to remove.

A further object of this invention is a method securing a screw-type fastener in a bore in a bone and subsequently completely removing this fastener from the bore.

SUMMARY OF THE INVENTION

A fastener for anchoring in a bore in a bone according to the invention has a screw extending along an axis and having a substantially cylindrical outer surface formed with a helical screwthread. The screw has at the screwthread a thread diameter and between the turns of the thread at the surface a root diameter smaller than the thread diameter. An anchor sleeve normally fitted in the bore and of an outside diameter corresponding generally to the diameter of the bore has an outer end formed with a laterally projecting rim normally lying against the bone around the bore, an outer end portion of an inside diameter greater than the root diameter but smaller than the thread diameter, and an inner end portion of an inside diameter smaller than the root diameter. Thus when the screw is threaded into the sleeve its thread cuts into the outer portion without substantially deforming and spreading same and into the inner portion with substantial outward deformation and spreading of same.

As a result the device gains an extremely good hold on the spongy interior of the bone. The sleeve is made of a resilient if not elastic synthetic resin, for instance a standard biological polyethylene, so that it can deform inward when withdrawn. More particularly according to this invention the sleeve is withdrawn when necessary by backing the screw off so it only engages in the outer portion and then simply pulling out the entire fastener, since the inner portion will be able to deform inward for such withdrawal.

According to another feature of this invention the sleeve has an inner end of an inside diameter generally corresponding to that of the outer end portion. The inner end portion lies between the inner end and the outer end portion. This inner end portion allows the screw to pass all the way through the sleeve without splitting it.

In addition according to this invention the sleeve is formed on the inner end portion with at least generally longitudinally extending and outwardly projecting ribs. These ribs can be wholly straight and longitudinal or can extend at least generally helically on the inner end portion.

So the sleeve, which is normally of a material transparent to X-rays, can be seen, its outer end portion has an outer surface clad with metal. This cladding can be a retrofitted sleeve or a vacuum-deposited film.

The sleeve of this invention is internally formed as a surface of revolution, the portions being internally cylindrical. In addition the screwthread has a sharp cutting edge like a self-tapping screw.

DESCRIPTION OF THE DRAWING

The above and other features and advantages will become more readily apparent from the following, reference being made to the accompanying drawing in which.

SPECIFIC DESCRIPTION

Figure 1:
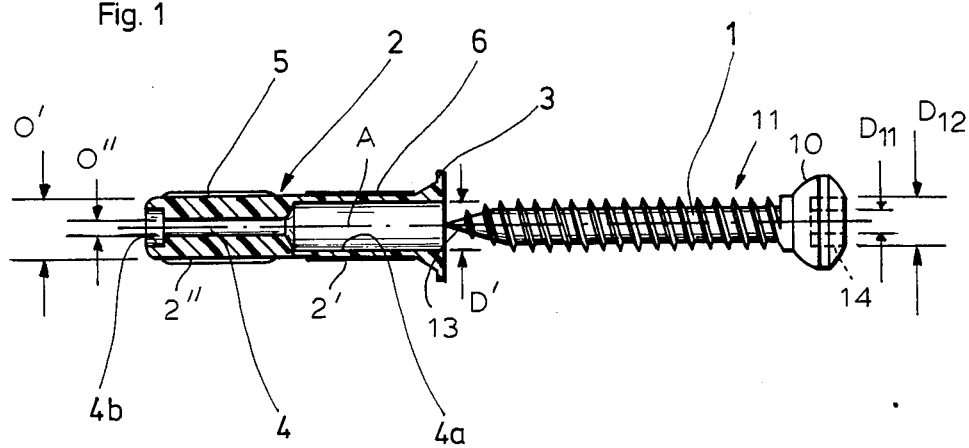
FIG. 1 is an exploded view in axial section through the fastener system according to this invention.

As seen in FIG. 1 a bone fastener system basically comprises a stainless-steel screw 1 and an anchor sleeve 2 of polyethylene of ultrahigh molecular weight. The screw 1 is centered on an axis A and has a cylindrical shaft 11 formed with a sharp-edged screwthread 12. The shaft 11 and thread 12 respectively define a shaft diameter $D_{11}$ and a larger thread diameter $D_{12}$. The tip 13 of the screw is pointed and the opposite outer end of the screw 1 has a head 10 formed with a hexagonal recess 14 centered on the axis A.

The sleeve 2 is also centered on the axis A and has an outer end formed with a radially projecting rim 3, and has an outer portion 2' and an inner portion 2''. The portion 2' has a cylindrical inner surface 4a of a diameter D' greater than the diameter $D_{11}$ but smaller than the diameter $D_{12}$ and the portion 2'' has a cylindrical inner surface 4 with a diameter D'' smaller than the diameter D11. The extreme inner end of the sleeve 2 has an inner surface 4b of the diameter D'.

In addition the sleeve 2 is formed at its inner end portion 2'' with longitudinal and helical ribs 5 and is provided on its inner portion 2' with a cladding 6 of stainless steel. This cladding 6 can be formed by a sleeve retrofitted to the portion 1' or by vacuum deposition thereon. It makes the sleeve 2 visible to X-rays, so its position and/or presence can be checked easily.

Figure 2:
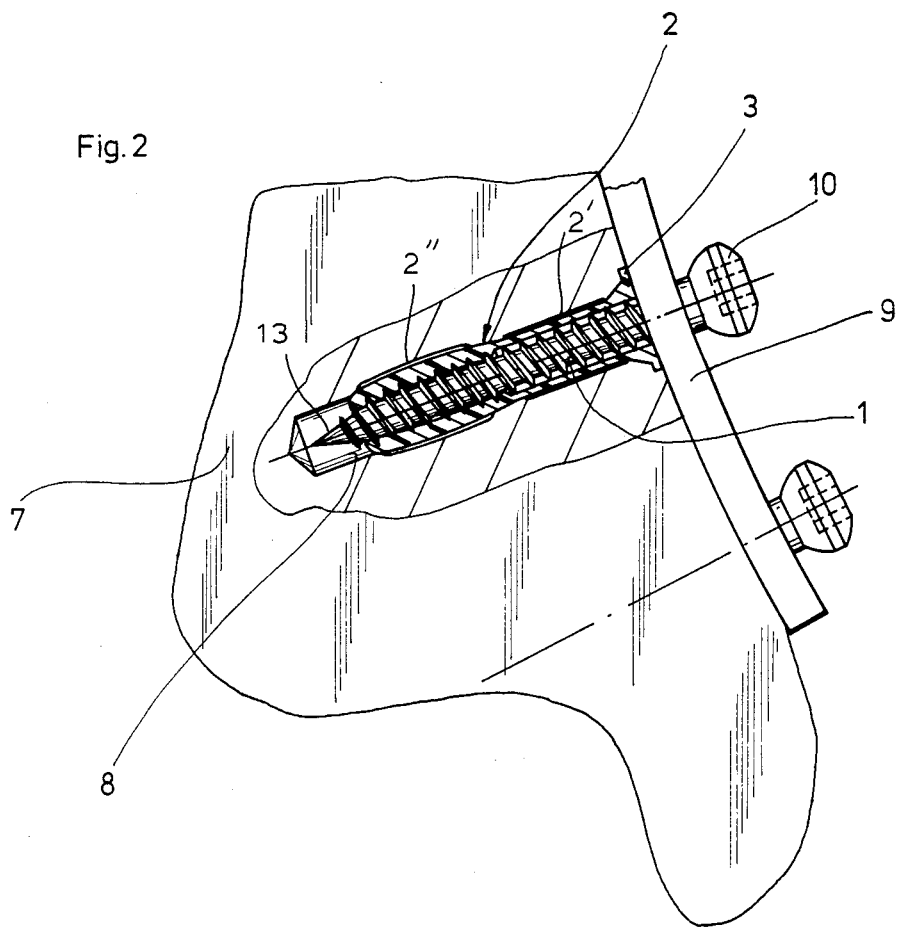
FIG. 2 is a partly sectional view illustrating use of the fastener system of this invention.

FIG. 2 shows how the fastener 1, 2 is installed in a bore 8 having a diameter equal to D' and a length slightly longer than that of the sleeve 2, with the rim 3 engaging flatly against or slightly recessed in the cortex of the tibia end 7 shown here. When the screw 1 is then threaded into the sleeve 2 the thread 12 bites slightly into the outer portion 2' without substantial outward deformation of this portion 2'. When, however, the screw bites into the portion 2" it swells it substantially outward, forcing the ridges 5 into excellent radial contact with the spongy interior of the bone 7. As a result there is excellent connection and holding of the screw 1 and sleeve 2 in the bore 7.

The tip 13 of the screw 1 passes out the extreme inner end of the sleeve 2 and the head 10 comes to lie against the outer face of a splint plate 9 here securing the medial malleolus on the bone 7. The resultant assembly is extremely strong, yet elastic enough that it has some give. Thus if momentarily stressed very greatly, the sleeve 2 will deform rather than the screw 1 tearing out.

To remove the assembly the screws 1 are backed out and the plate 9 removed. Then each screw 1 is threaded into the outer portion 2' only of the respective sleeve 2 and is pulled axially outward. Since the thread 12 is engaged in this portion 2' without enlarging it, this action will pull out the sleeve 2, as the spread but empty inner portion 2' can easily deflect back inward.

We claim:

1. A fastener for anchoring in a bore in a spongy interior of a bone, the fastener comprising:
    a screw extending along an axis and having a substantially cylindrical outer surface formed with a helical screwthread, the screw having at the screwthread a thread diameter and between the turns of the thread at the surface a root diameter smaller than the thread diameter;
    an anchor sleeve normally fitted in the bore and having an outside diameter corresponding generally to the diameter of the bore, the sleeve having
    an outer end formed with a laterally projecting rim normally lying against the bone around the bore,
    an outer portion with an inside diameter greater than the root diameter but smaller than the thread diameter, and
    an inner portion with an inside diameter smaller than the root diameter, said sleeve thereby being formed so that when the screw is threaded into the sleeve its thread cuts into the outer portion without substantially deforming and spreading same and into the inner portion with substantial outward deformation and spreading of same, said inner portion being formed resilient to deflect inward when said screw is unthreaded out of said inner portion thereby enabling said sleeve to be entirely withdrawn out of the bore when pulling out the screw;
    a rib projecting and extending generally longitudinally on said inner end portion so that said rib is forced into radial contact with a spongy interior of the bone when said inner end portion deforms outward and spreads by said screw threading into said inner end portion; and
    means for preventing said sleeve from splitting when said screw passes through said sleeve and including an inner end of said sleeve being formed with an inside diameter generally corresponding to said inside diameter of said outer end portion, said inner end being arranged so that said inner portion lies between said inner end and said outer portion.

2. The fastener defined in claim 1 wherein the ribs extend at least generally helically on the inner end portion.

3. The fastener defined in claim 1 wherein the outer end portion has an outer surface clad with metal.

4. The fastener defined in claim 1 wherein the sleeve is internally formed as a surface of revolution, the portions being internally cylindrical.

5. The fastener defined in claim 1 wherein the screwthread has a sharp cutting edge.

6. The fastener defined in claim 1 wherein the sleeve is of a deformable synthetic resin.

7. A method of mounting a screw-type fastener in and removing it from a bore in a spongy interior of a bone, the method comprising the steps of:
    threading a screw into and through an anchor sleeve in the bore, the screw extending along an axis and having a substantially cylindrical outer surface formed with a helical screwthread, the screw having at the screwthread a thread diameter and between the turns of the thread at the surface a root diameter smaller than the thread diameter, the anchor sleeve normally fitted in the bore and having an outside diameter corresponding generally to the diameter of the bore, the sleeve having
    an outer end formed with a laterally projecting rim normally lying against the bone around the bore,
    an outer portion with an inside diameter greater than the root diameter but smaller than the thread diameter,
    an inner portion with an inside diameter smaller than the root diameter, and
    an inner end having an inside diameter generally corresponding to said inside diameter of said outer portion, said inner end being arranged so that said inner portion lies between said inner end and said outer portion, the threading of the screw into and through the sleeve causing the thread to cut into the outer portion without substantially deforming and spreading same and into the inner portion with substantial outward deformation and spreading of same, the substantial outward deformation of the inner portion forcing a rib to radially engage with the spongy interior of the bone so as to solidly secure the sleeve in the bone while the engagement of the threads in the sleeve solidly secures the screw in the sleeve, the rib projecting and extending generally longitudinally on said inner portion;
    thereafter unthreading the screw out of the inner portion so that the screw partially engages only the outer portion of the sleeve and so that the inner portion deflects inward to allow pulling of the sleeve with the screw; and
    pulling the thus partially engaged screw away from the bone to thereby pull the sleeve out of the bore with the screw.

* * * * *